(12) United States Patent
Mateos et al.

(10) Patent No.: US 10,131,647 B2
(45) Date of Patent: Nov. 20, 2018

(54) CHROMENE DERIVATIVES SUBSTITUTED BY ALKOXIDE AS INHIBITORS OF THE TCR-NCK INTERACTION

(71) Applicant: ARTAX BIOPHARMA INC., Cambridge, MA (US)

(72) Inventors: Andrés Gagete Mateos, Cambridge, MA (US); Julio Castro Palomino, Barcelona (ES); Luc Marti Clauzel, Cambridge, MA (US); Damiá Tormo Carulla, Cambridge, MA (US)

(73) Assignee: Artex Biopharma Inc., Cambridge, MA (US)

( * ) Notice: Subject to any disclaimer, the term of this patent is extended or adjusted under 35 U.S.C. 154(b) by 0 days.

(21) Appl. No.: 15/029,042

(22) PCT Filed: Oct. 20, 2014

(86) PCT No.: PCT/IB2014/002171
§ 371 (c)(1),
(2) Date: Apr. 13, 2016

(87) PCT Pub. No.: WO2015/056085
PCT Pub. Date: Apr. 23, 2015

(65) Prior Publication Data
US 2016/0244423 A1    Aug. 25, 2016

(30) Foreign Application Priority Data
Oct. 18, 2013   (ES) .................................. 201331542

(51) Int. Cl.
*C07D 311/58*   (2006.01)
*C07D 311/74*   (2006.01)

(52) U.S. Cl.
CPC .......... *C07D 311/58* (2013.01); *C07D 311/74* (2013.01)

(58) Field of Classification Search
CPC ............................ C07D 311/58; C07D 311/74
USPC .................................................... 514/233.5
See application file for complete search history.

(56) References Cited

U.S. PATENT DOCUMENTS

| 8,614,231 B2 | 12/2013 | Alarcon et al. |
| 9,120,764 B2 | 9/2015 | Alarcon et al. |
| 2016/0251330 A1 | 9/2016 | Mateos et al. |

FOREIGN PATENT DOCUMENTS

| EP | 2354134 A1 | 8/2011 |
| WO | 2001034591 | 5/2001 |
| WO | 0208217 A2 | 1/2002 |
| WO | 2002092076 | 11/2002 |
| WO | 03062272 A1 | 7/2003 |
| WO | 2003096982 | 11/2003 |
| WO | 2007115820 A1 | 10/2007 |
| WO | 2010000900 A1 | 1/2010 |
| WO | 2010009069 A1 | 1/2010 |
| WO | 2012042078 A1 | 4/2012 |
| WO | WO 2012042078 A1 * | 4/2012 .......... C07D 311/58 |

OTHER PUBLICATIONS

PCT International Search Report dated Jan. 12, 2015 for International Application No. PCT/IB2014/002171, filed Oct. 20, 2014.
Spanish Search Report dated Jan. 20, 2015 for International Application No. 201331542, filed Oct. 18, 2013.
Alarcon et al., "Initiation of TCR signaling: regulation within CD3 dimers," Immunological Reviews, vol. 191, No Month Listed 2003 (pp. 38-46).
Borie et al., "Combined Use of the JAK3 Inhibitor CP-690,550 with Mycophenolate Mofetil to Prevent Kidney Allograft Rejection in Nonhuman Primates," Transplantation, vol. 80, No. 12, Dec. 27, 2005 (pp. 1756-1764).
Cetkovic-Cvrlje and Uckun, "Targeting Janus kinase 3 in the treatment of leukemia and inflammatory diseases," Archivum Immunologiae et Therapiae Experimentalis, vol. 52, No. 2, Mar.-Apr. 2004 (pp. 69-82).
Cetkovic-Cvrlje and Tibbles, "Therpaeutic Potential of Janus Kimase 3 (JAK3) Inhibitors," Current Pharmaceutical Design, vol. 10, No. 15, No Month Listed 2004 (pp. 1767-1784).
Das et al., "Discovery and SAR of 2-amino-5-(thioaryl)thiazoles as potent and selective Itk inhibitors," Bioorganic & Medicinal Chemistry Letters, vol. 16, May 2006 (pp. 3706-3712).
Gil et al., "Recruitment of Nck by CD3e Reveals a Ligand-Induced Conformational Change Essential for T Cell Receptor Signaling and Synapse Formation," Cell, vol. 109, Jun. 28, 2002 (pp. 901-912).
Glennon and Liebowitz, "Serotonin Receptor Affinity of Cathinone and Related Analogues," Journal of Medicinal Chemistry, vol. 25, No. 4, Apr. 1982 (pp. 393-397).

(Continued)

*Primary Examiner* — Yong L Chu
(74) *Attorney, Agent, or Firm* — Andrea L. C. Reid; Dechert LLP (57) ABSTRACT

The present invention relates to a group of compounds of formula (I) containing a chromene nucleus:

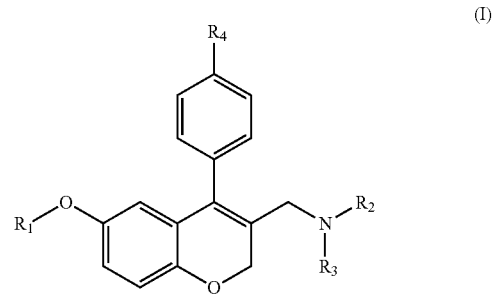

(I)

and that present the capacity to inhibit the proliferation of lymphocytes mediated by the Nck interaction with TCR, so that the present invention also relates to the use of these compounds for the treatment of diseases or conditions where said interaction triggers a complication such as transplant rejection reactions, immune or autoimmune diseases, inflammatory diseases or proliferative diseases.

22 Claims, 3 Drawing Sheets

(56) References Cited

OTHER PUBLICATIONS

Gonzalez-Rey et al., "Therapeutic Effect of Vasoactive Intestinal Peptide on Experimental Autoimmune Encephalomyelitis," American Journal of Pathology, vol. 168, No. 4, Apr. 2006 (1179-1188).
Holmdahl et al., "Collagen induced arthritis as an experimental model for rheumatoid arthritis," APMIS, vol. 97, No. 7, Jul. 1989 (pp. 575-584).
International Search Report issued by the Spanish Patent and Trademark Office as Searching Authority for International Patent Application No. PCT/ES2013/31543, dated Jan. 20, 2015 (4 pages).
Kaur et al., "Inhibitors of interleukin-2 inducible T-cell kinase as potential therapeutic candidate for the treatment of various inflammatory disease conditions," European Journal of Pharmaceutical Sciences, vol. 47, No. 3, Oct. 2012 (pp. 574-588).
Kremer et al., "A Randomized, Double-Blind, Placebo-Controlled Trial of 3 Dose Levels of CP-690,550 Versus Placebo in the Treatment of Active Rheumatoid Arthritis," American College of Rheumatology, 2006 Annual Scientific Meeting, Presentation No. L40, retrieved online <<https://acr.confex.com/acr/2006/webprogram/Paper6207.html>> accessed on Nov. 29, 2017 (2 pages).
Kudlacz et al., "The Novel JAK-3 Inhibitor CP-690550 Is a Potent Immunosuppressive Agent in Various Murine Models," American Journal of Transplantation, vol. 4, No. 1, Jan. 2004 (pp. 51-57).
Lin and Weiss, "T cell receptor signalling," Journal of Cell Science, vol. 114, No. 2, Jan. 2001 (pp. 243-244).
Malaviya et al., "Targeting Janus Kinase 3 in Mast Cells Prevents Immediate Hypersensitivity Reactions and Anaphylaxis," The Journal of Biological Chemistry, vol. 274, No. 38, Sep. 17, 1999 (pp. 27028-27038).
Malaviya et al., "Treatment of Allergic Asthma by Targeting Janus Kinase 3-Dependent Leukotriene Synthesis in Mast Cells with 4-(3',5'-Dibromom-4'-hydroxyphenyl)amino-6,7-dimethoxyquinazole (WHI-P97)," The Journal of Pharmacology and Experimental Therapeutics, vol. 295, No. 3, No Month Listed 2000 (pp. 901-926).
Matsumoto et al., "IgE Hyperproduction Through Enhanced Tyrosine Phosphorylation of Janus Kinase 3 in NC/Nga Mice, a Model for Human Atopic Dermatitis," The Journal of Immunology, vol. 162, No Month Listed 1999 (pp. 1056-1063).
Milici et al., "Cartilage Preservation by Inhibition of Janus Kinase 3 (JAK3) in a Murine Collagen-Induced-Arthritis (CIA) Model and Rat Adjuvant-Arthritis (AA) Model," American College of Rheumatology, 2006 Annual Scientific Meeting, Presentation No. 789, retrieved online <<https://acr.confex.com/acr/2006/webprogram/Paper4156.html>> accessed on Nov. 29, 2017 (1 page).
Muller-Ladner et al., "Activation of the IL-4 STAT Pathway in Rheumatoid Synovium," The Journal of Immunology, vol. 164, No Month Listed 2000 (pp. 3894-3901).
Narla et al., "Inhibition of Human Glioblastoma Cell Adhesion and Invasion by 4-(4'-Hydroxylphenyl)-amino-6,7-dimethoxyquinazoline (WHI-P131) and 4-(3'-Bromo-4'-hydroxylphenyl)-amino-6,7-dimethoxyquinazoline (WHI-P154)," Clinical Cancer Research, vol. 4, Oct. 1998 (pp. 2463-2471).
O'Shea et al., "A New Modality for Immunosuppression: Targeting the JAK/STAT Pathway," Drug Discovery, vol. 3, Jul. 2004 (pp. 555-564).

Paniagua et al., "Effects of JAK3 Inhibition with CP-690,550 on Immune Cell Populations and Their Functions in Nonhuman Primate Recipients of Kidney Allograft," Transplantation, vol. 80, No Month Listed 2005 (pp. 1283-1292).
Rousvoal et al., "Janus kinase 3 inhibition with CP-690,550 prevents allograft vasculopathy," European Society for Organ Transplantation, vol. 19, no Month Listed 2006 (pp. 1014-1021).
Roy et al., "Nck adaptors are positive regulators of the size and sensitivity of the T-cell repertoire," Proceedings of the National Academy of Science of the United States of America, vol. 107, No. 34, Aug. 2010 (pp. 15529-15534).
Saemann et al., "Janus kinase-3 (JAK3) inhibition: a novel immunosuppressive option for allogeneic transplantation," Transplant International, vol. 17, No. 9, Oct. 2004 (pp. 481-489).
Silva et al., "Immunotherapy for De Novo Renal Transplantation," Drugs, vol. 66, No. 13, No Month Listed 2006 (pp. 1665-1684).
Sudbeck et al., "Structure-based Design of Specific Inhibitors of Janus Kinase 3 as Apoptosis-inducing Antileukemic Agents," Clinical Cancer Research, vol. 5, Jun. 1999 (pp. 1569-1582).
Tibbles et al., "Role of a JAK3-dependent Biochemical Signaling Pathway in Platelet Activation and Aggregation," The Journal of biological Chemistry, vol. 276, No. 21, May 25, 2001 (pp. 17815-17822).
Trieu et al., "A Specific Inhibitor of Janus Kinase-3 Increases Survival in a Transgenic Mouse Model of Amyotrophic Lateral Sclerosis," Biochemical and Biophysical Research Communications, vol. 267, No. 1, No Month Listed 2000 (pp. 22-25).
Walker et al., "Changes in synovial tissue Jak-STAT expression in rheumatoid arthritis in response to successful DMARD treatment," Annals of the Rheumatic Diseases, vol. 65, No. 12, Dec. 2006 (pp. 1558-1564).
Francesco Leonetti et al; "Design, Synthesis, and 3D QSAR of Novel Potent and Selective Aromatase Inhibitors", Journal of Medicinal Chemistry, vol. 47, No. 27, Dec. 1, 2004 (Dec. 1, 2004). pp. 6792-6803, XP055096789, ISSN: 0022-2623, DOI: 10.1021/jm049535j *tables 3,4; compound 32*.
Higuchi, Takao. Prevention of Acute Lung Allograft Rejection in Rat by the Janus Kinase 3 Inhibitor, Tyrphostin AG490, The Second Department of Surgery and Department of Biochemistry, Fukuoka University School of Medicine, Fukuoka University School of Medicine, Fukuoka, Japan, Nov. 13, 2004, Copyright 2005 by the International Society for Heart and Lung Transplantation.
Database Registry, RN 340014-88-2, Retrieved from STN international [online]; retrieved on Jul. 8, 2013, Japanese Office Action of Japanese Application 2011-515490 dated Jul. 16, 2013.
American Diabetes Association, "complications", http://www.diabetes.org/living-with-diabetes/complications/, accessed Dec. 27, 2017 (Year: 2017).
Mayo Clinic, "Diabetes", https://www.mayoclinic.org/diseases-conditions/diabetes/symptoms-causes/syc-20371444, accessed Dec. 27, 2017 (Year: 2017).
Kannan et al., Pathophysiology, 2005, vol. 12., No. 3, pp. 167-181 (Year: 2005).
Asquith et al., Eur. J. Immunol., 2009, vol. 39, No. 8, pp. 2040-2044 (Year: 2009).
Moudgil et al., Curr. Rheumatol. Rep., 2011, vol. 13, No. 5, pp. 456-463 (Year: 2011).
International Search Report dated Oct. 5, 2009 in re PCT/ES2009/070239, filed on Jun. 18, 2009.

* cited by examiner

CHROMENE DERIVATIVES SUBSTITUTED BY ALKOXIDE AS INHIBITORS OF THE TCR-NCK INTERACTION

The present invention relates to a group of compounds containing a Chromene core and that have the ability to inhibit lymphocyte proliferation by blocking the interaction of TCR with Nck, so such compounds are useful for treating diseases or conditions where such interaction triggers a complication such as transplant rejection reactions, immune or autoimmune diseases, inflammatory diseases or proliferative diseases.

STATE OF THE ART

Autoimmune and inflammatory diseases such as asthma, multiple sclerosis, allergies, rheumatoid arthritis, Crohn's disease or psoriasis are a diverse group of diseases in which the adaptive immune system, particularly via T lymphocytes attack the body's own antigens. It is commonly accepted that T cells are at the center of all immunological mechanisms. T cells can recognize both foreign and self-antigens and activate the immune response against them. T cells recognize antigens via the T cell receptor (TCR), responsible for the transmission of signals to the cytoplasm. Indeed, the fact that the haplotype of the major histocompatibility complex (MHC) is the most important genetic risk factor to the human autoimmune diseases places T-cells in the center of all immunopathological events.

The T cell recognizes the antigen peptide associated with MHC (pMHC) via the T cell antigen receptor (TCR) and is able to translate the small differences in the chemical composition of the pMHC into different quantitative and qualitative results. While a variety of control mechanisms to prevent activation of T cells bearing TCRs with significant affinity for MHC loaded with self-peptides exists, including suppression of potentially auto-reactive T cells during maturation in the thymus, these mechanisms are somewhat insufficient in patients that develop autoimmune diseases and auto-reactive T cells are activated and expand, overcoming homeostatic controls.

Upon stimulation, the TCR is activated and undergoes a conformational change that results in the recruitment of different proteins forming the "TCR signalosome" responsible for signal transduction and cell activation. This complex includes the cytosolic protein Nck that binds to a PRS motif (proline-rich sequence) present in the CD3ε subunit of the T cell receptor. As a result, the TCR conformational change stabilizes and the activation signal is efficiently transmitted.

Current therapies for immune diseases appear as immunosuppressive strategies rather than tolerogenic/immunomodulatory approaches. Azathioprine, methotrexate, mycophenolate and cladribine are cytostatic. Other therapies force the depletion of T cells (Alemtuzumab, anti-CD52) or their retention in lymph nodes (Fingolimod). Alternatively, indirect modulation of the immune system is also being used as a powerful strategy (BG-12). Therefore, despite the central role of TCR signal for activating T cells in autoimmune diseases, recent efforts to modulate activation of the T cells are focused in modulating co-stimulatory signals, cytokine receptors, etc. with the consequent lack of specificity and a large number of associated side effects.

In order to develop a specific immunomodulatory therapy, many efforts have been focused on characterizing the role of Nck in T cell activation by means of many different research groups. Nck has been attributed an important role in the function of mature T cells through studies in knock-out mice lacking Nck1 in all tissues and lacking Nck2 conditionally only on T cells. In these models, the number of peripheral T cells expressing a TCR with low avidity for self antigens fell sharply, and a general deterioration in the activation of T cells by stimulation with weak antigens was observed. Moreover, the importance of Nck was also addressed by generating bone marrow chimeras showing that the PRS motive (Nck binding site in the TCR) is important for the activation of mature T cells by weak agonists but not strong ones. Similarly, mutation of the PRS sequence altered the ability of mice to activate an adaptive immune response in vivo. Furthermore, an inhibitor peptide with high affinity for the SH3.1 domain of Nck alters the assembly of the TCR signalosome, suggesting that the recruitment of Nck is a critical early step in TCR signaling, which represents a target for the modulation of the immune response.

The document WO2010/064707 describes a series of compounds derived from 2H-chromene for the prevention or treatment of an disease induced by an undesired lymphocytes infiltration mediated by the sphingosine-1-phosphate receptor (S1P1).

The document WO2012/042078 also describes chromene derivatives with inhibitory capacity of the TCR-Nck interaction in T cells and their use for the treatment of autoimmune diseases, inflammatory diseases or transplant rejection.

It would therefore be desirable to provide novel compounds which are capable of inhibiting TCR-Nck interaction in T lymphocytes, and that are a good drug candidate. The compounds should exhibit good activity on in vivo pharmacological trial, good oral absorption when administered orally as well as being metabolically stable and having a favourable pharmacokinetic profile. Moreover, compounds should not be toxic and present minimal side effects.

DESCRIPTION OF THE INVENTION

The compounds described below have a high ability to inhibit the interaction between TCR-Nck, so they are useful for treating diseases or disorders in which a hyperproliferation of T lymphocytes occurs. Moreover, the compounds of the present invention present better bioavailability than structurally similar known compounds and with the same capacity of inhibition of TCR-Nck, which is a distinct advantage of the compounds of the invention in its use as drugs.

The first aspect of the present invention relates to a compound of formula (I) or a or a pharmaceutically acceptable salt, isomer or solvate thereof wherein:

$R_1$ is selected from hydrogen, substituted or not substituted $C_1$-$C_6$ alkyl, substituted or not substituted $C_3$-$C_6$ cycloalkyl, substituted or not substituted aryl or substituted or not substituted heteroaryl, —$COR_5$, —$C(O)OR_5$, —$C(O)NR_5R_6$, —$CNR_5$;

$R_2$ and $R_3$ are independently selected from hydrogen, substituted or not substituted $C_1$-$C_6$ alkyl, substituted or not substituted $C_3$-$C_6$ cycloalkyl, substituted or not substituted aryl, substituted or not substituted heteroaryl, —$COR_7$, —$O(O)OR_7$, —$C(O)NR_7R_8$, —$CNR$, —$OR_7$, —$NR_7R_8$ and —$NR_7C(O)R_8$:

or $R_2$ and $R_3$ form, together with the nitrogen atom they are bound to, a substituted or not substituted heterocycle:

$R_4$ is halogen;

$R_5$, $R_6$, $R_7$ and $R_8$ are independently selected from hydrogen. $C_1$-$C_4$ alkyl, $C_3$-$C_6$ cycloalkyl, aryl, heteroaryl and halogen.

with the condition that the compound of formula (I) is not 1-((4-(4-fluorophenyl)-6-methoxy-2H-chromene-3-yl)methyl)pyrrolidine.

The term "alkyl" refers, in the present invention, to radicals of hydrocarbonated chains, linear or branched, having 1 to 6 carbon atoms, and preferably 1 to 4, and bound to the rest of the molecule by a single bond, for example, methyl, ethyl, n-propyl, i-propyl, n-butyl, tort-butyl, sec-butyl, n-pentyl, n-hexyl, etc. The alkyl groups may be optionally substituted by one or more substituents such as halogen, hydroxyl, alkoxyl, carboxyl, carbonyl, cyano, acyl, alkoxycarbonyl, amino, nitro, mercapto and alkylthio.

The term "cycloalkyl" refers, in the present invention, to a stable 3 to 6-membered monocyclic radical, preferably 3-membered, saturated or partially unsaturated, and which consists only of carbon and hydrogen atoms, such as cyclopropyl, cyclopentyl, cyclohexyl and which may optionally be substituted by one or more groups such as alkyl, halogen, hydroxyl, alkoxyl, carboxyl, cyano, carbonyl, acyl, alkoxycarbonyl, amino, nitro, mercapto and alkylthio.

The term "aryl" refers, in the present invention, to an aromatic carbocyclic chain having 6 to 18 carbon atoms, preferably 6 to 14 carbon atoms and more preferably 6 to 8, and may be made of a single or multiple rings, in the latter case with separated and/or fused rings. Nonlimiting examples of the aryl group are phenyl, naphthyl, indenyl, etc. Preferably the aryl group is a phenyl or naphthyl. The aryl groups may be optionally substituted by one or more 5 substituents such as alkyl, halogen, hydroxyl, alkoxyl, carboxyl, carbonyl, cyano, acyl, alkoxycarbonyl, amino, nitro, mercapto and alkylthio.

The term "heteroaryl" refers to an aryl group containing at least one heteroatom selected from the following group: nitrogen, oxygen or sulfur.

The term "heterocycle" refers, in the present invention, to a stable monocyclic or bicyclic radical of 3 to 15 members that is unsaturated, saturated or partially saturated, and which consists of carbon atoms and at least one heteroatom selected from the following group: nitrogen, oxygen or sulfur. Preferably, it has 4 to 8 members with one or more heteroatoms, more preferably from 5 to 6 members with one or more heteroatoms. Examples of heteroaryl may be, not limited to: azepines, indoles, imidazoles, isothiazoles, thiadiazoles, furan, tetrahydrofuran, benzimidazole, benzothiazole, piperidine, pyrrolidine, piperazine, purine, quinoline. Preferably, the heterocyclic group is pyrrolidine or piperazine. The heterocycle groups may be optionally substituted in any of their positions by one or more substituents such as alkyl, halogen, hydroxyl, alkoxyl, carboxyl, carbonyl, cyano, acyl, alkoxycarbonyl, amino, nitro, mercapto and alkylthio.

"Halogen" refers to fluorine, chlorine, bromine or iodine.

In a preferred embodiment, $R_1$ is a substituted or not substituted $C_1$-$C_4$ alkyl. In a more preferred embodiment, $R_1$ is —$CH_3$.

In another more preferred embodiment, $R_1$ is a $C_1$-$C_4$ alkyl substituted by a $C_3$-$C_6$ cycloalkyl. In an even more preferred embodiment, $R_1$ is a —$CH_2$-cyclopropyl group.

In another preferred embodiment, $R_1$ is a $C_1$-$C_4$ alkyl substituted by at least one fluorine. In a more preferred embodiment $R_1$ is selected from the —$CHF_2$ or —$CF_3$ groups.

In another preferred embodiment, $R_1$ is hydrogen.

In another preferred embodiment, $R_2$ is H.

In another preferred embodiment, $R_3$ is a substituted or not substituted $C_1$-$C_4$ alkyl. In a more preferred embodiment, $R_3$ is a —$CH_2CH_3$ group.

In another more preferred embodiment, $R_3$ is a $C_1$-$C_4$ alkyl substituted by a group —NR'R", wherein R' and R" are independently selected from H or $C_1$-$C_4$ alkyl. In a more preferred embodiment, $R_3$ is the —$CH_2$—$CH_2$—$N(CH_3)_2$ group.

In another preferred embodiment, $R_2$ and $R_3$ form a substituted or not substituted saturated 5-membered heterocyclic.

In another preferred embodiment, $R_2$ and $R_3$ form a saturated 6-membered heterocycle optionally substituted.

In a more preferred embodiment, the saturated heterocycle is substituted by a $C_1$-$C_4$ alkyl in at least one of its positions.

In another more preferred embodiment, the saturated 6-membered heterocycle containing inserted an additional N or O atom. In an even more preferred embodiment, the N is substituted by a $C_1$-$C_4$ alkyl.

In another preferred embodiment, $R_3$ is a saturated 6-membered heterocycle containing inserted an additionally N atom unsubstituted or substituted by a $C_1$-$C_4$ alkyl.

In another preferred embodiment, $R_4$ is fluorine.

In a preferred embodiment, the compound of formula (I) is selected from the following list:

4-(4-fluorophenyl)-3-(pyrrolidine-1-ylmethyl)-2H-chromen-6-ol (AX-01), 1-((6-(difluoromethoxy)-4-(4-fluorophenyl)-2H-chromen-3-yl)methyl)pyrrolidine (AX-02)

1-((4-(4-fluorophenyl)-6-(trifluoromethoxy)-2H-chromen-3-yl)methyl)pyrrolidine (AX-03)

1-((6-(cyclopropylmethoxy)-4-(4-fluorophenyl)-2H-chromen-3-yl)methyl)pyrrolidine (AX-04)

1-((4-(4-fluorophenyl)-6-methoxy-2H-chromen-3-yl)methyl)-4-methylpiperazine (AX-9)

$N^1$-((4-(4-fluorophenyl)-6-methoxy-2H-chromen-3-yl)methyl)-$N^2$,$N^2$-dimethylethane-1,2-diamine (AX-10)

4-((4-(4-fluorophenyl)-6-methoxy-2H-chromen-3-yl)methyl)morpholine (AX-11)

N-((4-(4-fluorophenyl)-6-methoxy-2H-chromen-3-yl)methyl)-ethanamine (AX-12)

1-((6-(diflueromethoxy)-4-(4-fluorophenyl)-2H-chromen-3-yl)methyl)-4-methylpiperazine (AX-17)

$N^1$-((6-(difluoromethoxy)-4-(4-fluorophenyl)-2H-chromen-3-yl)methyl)-$N^2$,$N_2$-dimethylethane-1,2-diamine (AX-18)

$N^1$-((4-(4-fluorophenyl)-6-(trifluoromethoxy)-2H-chromen-3-yl)methyl)-$N^2$,$N^2$-dimethylethane-1,2-diamine (AX-26)

4-((4-(4-fluorophenyl)-6-(trifluoromethoxy)-2H-chromen-3-yl)methyl)morpholine (AX-27)
N-((4-(4-fluorophenyl)-6-(trifluoromethoxy)-2H-chromen-3-yl)methyl)ethanamine (AX-28)
1-((6-(cyclopropylmethoxy)-4-(4-fluorophenyl)-2H-chromen-3-yl)methyl)-4-methylpiperazine (AX-33)
$N^1$-((6-(cyclopropylmethoxy)-4-(4-fluorophenyl)-2H-chromen-3-yl)methyl)-$N^2$,$N^2$-dimethylethane-1,2-diamine (AX-34)
4-((6-(cyclopropylmethoxy)-4-(4-fluorophenyl)-2H-chromen-3-yl)methyl)morpholine (AX-35)
N-((6-(cyclopropylmethoxy)-4-(4-fluorophenyl)-2H-chromen-3-yl)methyl)ethanamine (AX-36)

In another preferred embodiment, the compound of formula (I) is selected from the following list:
1-((4-(4-fluorophenyl)-6-methoxy-2H-chromen-3-yl)methyl)-4-methylpiperazine (AX-9)
$N^1$-((4-(4-fluorophenyl)-6-methoxy-2H-chromen-3-yl)methyl)-$N^2$,$N^2$-dimethylethane-1,2-diamine (AX-10)
1-((6-(cyclopropylmethoxy)-4-(4-fluorophenyl)-2H-chromen-3-yl)methyl)-4-methylpiperazine (AX-33)
4-((4-(4-fluorophenyl)-6-(trifluoromethoxy)-2H-chromen-3-yl)methyl)morpholine (AX-27)
4-((6-(cyclopropylmethoxy)-4-(4-fluorophenyl)-2H-chromen-3-yl)methyl)morpholine (AX-35)
N-((6-(cyclopropylmethoxy)-4-(4-fluorophenyl)-2H-chromen-3-yl)methyl)ethanamine (AX-36)

Another aspect of the invention relates to the use of the compound of formula I as described above for the manufacture of a medicament.

Another aspect of the invent on relates to the use of the compound of formula (I) as described above for the manufacture of a medicament for treating diseases or disorders mediated by TCR-Nck interaction in T lymphocytes.

Throughout this description, the terms "treatment" of a disease, "treat" a disease or other grammatically related expressions refer to a curative treatment as well as a palliative treatment or prophylactic treatment of such disease.

In a preferred embodiment, the disease or disorder mediated by the TCR-Nck interaction in T lymphocytes is selected among transplant rejection, immune, autoimmune and inflammatory diseases, neurodegenerative diseases, hematological diseases and proliferative diseases.

In a more preferred embodiment, the disease or disorder mediated by the TCR-Nck interaction in T lymphocytes is selected from transplant rejection, rheumatoid arthritis, psoriatic arthritis, psoriasis, Type I diabetes, complications associated with diabetes, multiple sclerosis, systemic lupus erythematosus, atopic dermatitis, mast cell-mediated allergic reactions, leukemias, lymphomas and thromboembolic and allergic complications associated with leukemias and lymphomas.

Another aspect of the invention refers to a compound of formula (I) for its use in the treatment of diseases or disorders mediated by the TCR-Nck interaction in T lymphocytes.

Another aspect of the invention relates to a pharmaceutical composition comprising a compound of formula (I) as described above and one or more pharmaceutically acceptable excipients.

The compounds described in the present invention, its pharmaceutically acceptable salts and/or solvates like the pharmaceutical compositions that contain them can be used together with other additional drugs to provide a combination therapy. Said additional drugs can be part of the same pharmaceutical composition or, alternatively, can be provided in form of a separate composition for its simultaneous administration or not to the pharmaceutical composition comprising a compound of formula (I), or an isomer, solvate or a salt pharmaceutically acceptable thereof.

Unless otherwise indicated, the compounds of the invention also include compounds which differ only in the presence of one or more isotopically enriched atoms. For example, compounds having said structure, except for the replacement of a hydrogen by a deuterium or tritium, or the replacement of a carbon by a $^{13}$C or $^{14}$C-enriched carbon or a $^{15}$N-enriched nitrogen, are within the scope of this invention.

The compounds of formula (I) for therapeutic use are prepared in solid form or aqueous suspension, in a pharmaceutically acceptable diluent. These preparations may be administered by any suitable route of administration, for which said preparation will be formulated in the pharmaceutically adequate method for the chosen route of administration. In a particular embodiment, administration of the compound of formula (I) provided by this invention is carried out by oral, topical, rectal or parenteral (including subcutaneous, intraperitoneal, intradermal, intramuscular, intravenous, etc.) route. A review of the different pharmaceutical forms of administering medicaments and of excipients necessary for obtaining them can be found, for example, in the "Treaty of Galenic Pharmacy" C. Fauli i Trillo, 1993 Luzén 5, SA Ediciones, Madrid, or in other common or similar to the Spanish, European or American Pharmacopoeias.

For its application in therapy, the compounds of formula (I), their isomers, salts or solvates, will be found, preferably, to be in a acceptable or substantially pure pharmaceutical form, i.e., having a pharmaceutically acceptable level of purity excluding pharmaceutical additives that are normal such as diluents and carriers, and not including material considered toxic at levels of normal dosage. The purity levels for the active substance are preferably above 50%, more preferably above 70%, more preferably greater than 90%. In a preferred embodiment, they are above 95% of the compound of formula (I), or of its isomers, salts or solvates.

The compounds of the invention may be in crystalline form as free compounds or as solvates and it is intended that both forms are within the scope of the present invention. Here, the term "solvate" as used herein, includes both pharmaceutically acceptable solvates, i.e. solvates if the compound of formula (I) which can be used in the manufacture of a medicament, as pharmaceutically unacceptable solvates, which may be useful in the preparation of salts or solvates that are pharmaceutically acceptable. The nature of the pharmaceutically acceptable solvate is not critical provided that it is pharmaceutically acceptable. In a particular embodiment, the solvate is a hydrate. The solvates may be obtained by conventional methods of solvation well known by technicians of the subject.

The compounds of the present invention represented by formula (I), and specifically, the specific compounds belonging to this general formula described previously may include isomers, depending on the presence of multiple bonds (e.g. Z, E), including optical isomers or enantiomers, depending on the presence of chiral centers. The isomers, enantiomers or individual diastereoisomers and mixtures thereof fall within the scope of the present invention. The individual enantiomers or diastereoisomers, like their mixtures, may be separated by conventional techniques.

Another aspect of the invention is a method of treating diseases or disorders mediated by the TCR-Nck interaction in T cells which comprises administering a therapeutically effective amount of a compound of formula (I) to a patient in need thereof.

As used herein, the term "therapeutically effective amount" refers to the amount of active compound sufficient to produce the desired effect in which the symptoms of the disease are attenuated. The dose should not be used in amounts that cause unwanted side effects, in which clinical assessment makes them adverse and them therapeutically untreatable. Generally the dosage will vary with the age, condition, sex and extent of disease in the patient as well as the route and frequency of administration and will be determined in each case.

Another aspect of the invention relates to a process of obtaining a compound of formula (I) as described above comprising the following steps:
a) reacting a compound of formula (II) with a compound of formula (III) and a compound of formula (IV)

where $R_1$, $R_2$, $R_3$ and $R_4$ have the same meaning as in claim 1 and b) transforming, in one or more steps, a compound of formula (II) to another of formula (I)

Throughout the description and claims the word "comprise" and its variants are not intended to exclude other technical features, additives, components or steps. To experts of the subject, other objects, advantages and features of the invention will become apparent in part from the description and practice of the invention. The following examples and figures are provided by way of illustration, and are not intended to be limiting of the present invention.

EXAMPLES

The invention will be illustrated by tests performed by the inventors, which shows the effectiveness of the compounds of the invention.

Example 1: Synthesis of the Compounds of the Invention

Synthesis Scheme of AX-101

Synthesis of AX-101 (free base): To a solution of AX-24.HCl (1 g, 1 eq.) in dry DCM (10 ml), BBr$_3$ (0.79 g, 1.2 eq.) was added drop by drop at −78° C. and stirred at RT overnight. The reaction was monitored by TLC. After completion, the reaction mixture was poured into a cold solution of saturated sodium bicarbonate and extracted with DCM (2×20 ml). The combined organic layer was washed with water (20 ml), saline solution (10 ml) and dried over Na$_2$SO$_4$. Purification of the crude product by column chromatography (100% ethyl acetate) yielded 0.5 g of the desired product (light brown solid) with a purity of 97.8% by HPLC. $^1$NMR (400 MHz, DMSO-d$^6$): δ 8.80 (s, 1H), 7.31-727 (m, 2H), 7.20-7.17 (m, 2H), 6.68-6.66 (d, 2H), 6.51-6.28, (dd, 1H), 5.93 (s, 1H), 473 (s, 1H), 2.96 (s, 2H), 2.29 (b, 4H), 1.61 (b, 4H). Theoretic MS for C$_{20}$H$_{20}$FNO$_2$: 325.4; M$^+$+1 found: 326.1.

Synthesis Scheme of AX-104

-continued

AX-104

Synthesis of AX-104: To the mixture of AX-101 (0.7 g, 1 eq.), K₂CO₃ (1 g, 3 eq.), cyclopropyl methyl bromide (1.16 g, 4 eq.) in DMF (10 ml) and acetone (20 ml), and tetramethylammonium bromide (0.1 g, catalytic) were added. The resulting reaction mixture was heated at 80° C. overnight. The reaction was controlled by TLC. After completion, the reaction mixture was poured into cold water (40 ml) and extracted with ethyl acetate (3×20 ml). The combined organic layer was washed with water (2×15 ml), saline solution (10 ml) and dried over anhydrous sodium sulfate. Purification of the crude product by column chromatography (20% ethyl acetate in hexane) yielded 0.1 g of the desired product with a purity of 96% by HPLC, ¹H NMR (400 MHz, DMSO-d⁶): δ 7.31-7.27 (m, 2H), 7.21-7.19 (m, 2H), 6.78-6.76 (d, 2H), 6.70-6.67 (dd, 1H), 5.97-5.96 (d, 1H), 3.58-3.56 (d, 2H), 2.97 (s, 2H), 2.3 (b, 4H), 1.61 (b, 4H), 1.8-12 (m, 4H), 0.49-0.44 (m, 2H), 0.21-0.18 (m, 2H), Theoretic MS for C₂₄H₂₆FNO₂: 379.5, M⁺+ found 1, 380.1.

Synthesis Scheme for AX-133 to AX-136

Synthesis of Compound B: To a solution of compound A (10 g, 1 eq,) in dry DCM (150 ml), BBr$_3$ (11.4 g. 1.3 eq.) was added drop by drop at 0° C. and stirred at RT overnight. The reaction was controlled by TLC. After completion, the reaction mixture was poured into cold water and extracted with DCM (2×150 ml). The combined organic layer was washed with water (2×70 ml), saline solution (20 ml) and dried over Na$_2$SO$_4$. Purification of the crude product by column chromatography (40% ethyl acetate in hexane) yielded 4.7 g of the desired product. Theoretic MS for C$_{16}$H$_{11}$FO$_3$: 324.12, M$^+$+1 found, 325.2.

Synthesis of Compound C: To the mixture of Compound B (5.5 g, 1 eq), K$_2$CO$_3$ (11.2 g 4 eq.), cyclopropylmethyl bromide (5.5 g, 2 eq.) in DMF (50 ml), and tetramethylammonium bromide (0.1 g, catalytic) was added. The resulting reaction mixture was heated at 75° C. overnight. The reaction was controlled by TLC. After completion the mixture was poured into cold water (100 ml) and extracted with ethyl acetate (3×70 ml). The combined organic layer was washed with water (2×40 ml), saline solution (20 ml) and dried over anhydrous sodium sulfate. Purification of the crude product by column chromatography (10% ethyl acetate in hexane) yielded 1.7 g of the desired product. Theoretic MS for C$_{20}$H$_{17}$FO$_3$: 324.12, M$^+$+1 found, 325.2.

Synthesis of Compound D: To the mixture of Compound C (3 g, 1 eq), sodium borohydride (0.17 g, 0.5 eq.) was added dropwise in toluene (20 ml), methanol (2 ml) to RT and stirred at this temperature for 2 h. The reaction was monitored by TLC. After completion, the mixture was poured into cold water (100 ml) and extracted with ethyl acetate (2×30 ml). The combined organic layer was washed with water (20 ml), saline solution (10 ml) and dried over anhydrous sodium sulfate. Evaporation of the organic layer under reduced pressure yielded 2.7 g of the desired product. This material was taken directly to the next step without purification and analysis.

Synthesis of Compound E: To a mixture of Compound D (3.5 g, 1 eq), sodium borohydride was added dropwise in toluene (30 ml), thionyl chloride (1.78 g, 1.4 eq) at 0° C. and stirred at RT for 2 h. The reaction was monitored by TLC. After completion, the mixture was poured into iced water (25 ml) and extracted with ethyl acetate (2×25 ml). The combined organic layer was washed with water (30 ml), saline solution (10 ml) and dried over anhydrous sodium sulfate. Evaporation of the organic layer under reduced pressure (vacuum evaporation) yielded 3.4 g of raw product. This material was taken directly to the next step without purification and analysis.

Synthesis of AX-133: Mixture of Compound E (0.3 g, 1 eq), K$_2$CO$_3$ (0.36 g of 3 eq), N-methyl piperazine (0.13 g, 1.5 eq) in diisopropyl ether (15 ml) was was stirred at RT overnight. The reaction was monitored by TLC. After completion, the mixture was poured into cold water (20 ml) and extracted with ethyl acetate (2×30 ml). The combined organic layer was washed with water (20 ml), saline solution (10 ml) and dried over anhydrous sodium sulfate. Purification of the crude product by column chromatography (10% methanol in DCM) yielded 40 mg of the desired product with a purity of 92.9% by HPLC. $^1$H NMR (400 MHz, CDCl$_3$): δ 7.11-7.2 (m, 4H), 6.78-6.75 (d, 1H), 6.65-6.63 (dd, 1H), 6.15-6.14 (d, 1H), 4.78 (s, 2H), 3.57-3.55 (d, 2H), 2.97 (s, 2H), 2.52 (b, 8H), 1.23 (s, 3H), 1.14-1.8 (m, 1H), 0.56-0.52 (m, 2H), 0.24-0.020 (m, 2H). Theoretic MS for C$_{25}$H$_{29}$FN$_2$O$_2$: 408.51, M$^+$+1 found 409.2.

Synthesis of AX-134: Mixture of Compound E (0.3 g, 1 eq.), K$_2$CO$_3$ (0.55 g 5 eq.), N,N-dimethylethylenediamine (0.28 g, 4 eq.) in diisopropyl ether (15 mL) was refluxed for 2 h. The reaction was monitored by TLC. After completion, the mixture was poured into cold water (20 ml) and extracted with ethyl acetate (2×30 ml). The combined organic layer was washed with water (20 ml), saline solution (10 ml) and dried over anhydrous sodium sulfate. Purification of the crude product by column chromatography (12% methanol in DCM) yielded 80 mg of the desired product with a purity of 93.2% by HPLC. $^1$H NMR (CDCl$_3$): δ 7.16-7.8 (m, 4H), 6.80-677 (d, 1H), 6.68-6.63 (dd, 1H), 6.18-6.17 (d, 1H), 4.85 (s, 2H), 3.60-3.58 (d, 2H), 3.19 (s, 2H), 2.55-2.52 (t, 2H), 2.34-231 (t, 2H), 2.18 (b, 5H), 1.14-1.12 (m, 1H), 0.57-0.55 (m, 2H), 0.25-0.24 (m, 2H). Theoretic MS for C$_{24}$H$_{29}$FN$_2$)$_2$: 3965, M$^+$+1 found, 397.2.

Synthesis of AX-135: Mixture of Compound E (0.2 g, 1 eq), K$_2$CO$_3$ (0.24 g of 3 eq), morpholine (0.1 g, 2 eq) in diisopropyl ether (15 ml) was refluxed for 2 h. The reaction was monitored by TLC. After completion, the mixture was poured into cold water (20 ml) and extracted with ethyl acetate (2×20 ml). The combined organic layer was washed with water (20 ml), saline solution (10 ml) and dried over anhydrous sodium sulfate. Purification of the crude product by column chromatography (30% ethyl acetate in hexane) yielded 45 mg of the desired product with a purity of 95.8% by HPLC. $^1$H NMR (DMSO-d$^6$): δ 7.37-7.26 (t, 2H), 7.21-7.16 (m, 2H), 6.78-6.76 (d, 1H), 671-6.68 (dd, 1H), 5.97-5.96 (d, 1H), 4.75 (s, 2H), 3.58-3.56 (d, 2H), 3.52-3.50 (m, 2H), 2.87 (s, 2H), 2.21 (b, 4H), 1.8-1.3 (m, 1H), from 0.49 to 0.44 (m, 2H), 0.21 to 0.17 (m, 2H). Theoretic MS for C$_{24}$H$_{26}$FNO$_3$: 395.47, M$^+$+1 found, 396.1.

Synthesis of AX-136; Mixture of Compound E (0.3 g, 1 eq), K$_2$CO$_3$ (0.36 g of 3 eq), ethylamine hydrochloride (0.22 g, 3 eq) in DMF (10 ml) was stirred at RT overnight. The reaction was monitored by TLC. After completion, the mixture was poured into cold water (20 ml) and extracted with ethyl acetate (3×20 ml). The combined organic layer was washed with water (2×15 ml), saline solution (10 ml) and dried over anhydrous sodium sulfate. Purification of the crude product by column chromatography (5% methanol in DCM) yielded 50 mg of the desired product with a purity of 92.2% by HPLC. $^1$H NMR (CDCl$_3$): δ 7.16-7.9 (m, 4H), 6.80-6.78 (d, 1H), 6.68-6.63 (dd, 1H), 6.19-6.17 (s, 1H), 4.83 (s, 2H), 3.60-3.58 (d, 2H), 3.2 (s, 2H), 2.54-2.49 (q, 2H), 1.16-1.12 (m, 1H), 1.02-0.98 (t, 3H), 0.59 to 0.54 (m, 2H), 0.27-0.23 (m, 2H). Theoretic MS for $C_{24}H_{26}FNO_3$; 353.43; M-44.3 found, 309.1 (Ethyl amine group cleaves mass).

Synthesis Scheme for AX-102, AX-117 and AX-118

Synthesis of Compound B: A mixture of Compound A (3 g, 1 eq), $K_2CO_3$ (3.06 g, 2 eq), ethyl chlorodifluoroacetate (2.2 g, 1.3 eq) in DMF (20 ml), was heated at 75° C. overnight. The reaction was monitored by TLC. After completion, the mixture was poured into cold water (50 ml) and extracted with ethyl acetate (3×50 ml). The combined organic layer was washed with water (2×30 ml), saline solution (20 ml) and dried over anhydrous sodium sulfate. Purification of the crude product by column chromatography (10% ethyl acetate in hexane) yielded 1 g of the desired product, $^1H$ NMR (DMSO-$d^6$) Theoretical MS for $C_{17}H_{11}F_3NO_3$: 320.26; $M^+$+1 found, 321.1.

Synthesis of Compound C: To the mixture of Compound B (1 g, 1 eq), sodium borohydride (0.05 g, 0.5 eq) in toluene (10 ml) and methanol (2 ml) was added dropwise at RT and stirred at this temperature for 2 h. The reaction was monitored by TLC. After completion, the mixture was poured into cold water (30 ml) and extracted with ethyl acetate (2×30 ml). The combined organic layer was washed with water (15 ml), saline solution (10 ml) and dried over anhydrous sodium sulfate. Evaporation of the organic layer under reduced pressure (vacuum evaporation) yielded 0.9 g of the desired product. This material was taken directly to the next step without purification and analysis.

Synthesis of Compound D: To a mixture of Compound C (0.9 g, 1 eq) in toluene (20 ml), thionyl chloride (0.43 g, 1.3 eq) was added drop by drop at 0° C. and stirred at RT for 2 h. The reaction was monitored by TLC. After completion, the mixture was poured into cold water (20 ml) and extracted with ethyl acetate (2×30 ml). The combined organic layer was washed with water (20 ml), saline solution (10 ml) and dried over anhydrous sodium sulfate. Evaporation of the organic layer under reduced pressure (vacuum evaporation) yielded 0.9 g of raw product. This material was taken directly to the next step without purification and analysis.

Synthesis of AX-102: Mixture of Compound D (0.25 g, 1 eq), $K_2CO_3$ (0.5 g, 5 eq), and pyrrolidine (0.15 g, 3 eq) in diisopropyl ether (15 ml) was heated at 60° C. for 2 h. The reaction was monitored by TLC. After completion the mixture was poured into cold water (20 ml) and extracted with ethyl acetate (2×25 ml). The combined organic layer was washed with water (20 ml), saline solution (10 ml) and dried over anhydrous sodium sulfate. Purification of the crude product by column chromatography (40% ethyl acetate in hexane) gave 50 mg of the desired product with 94.4% HPLC purity 30. $^1$H NMR (DMSO-d$^6$)$^1$H NMR (CDCl$_3$) δ 7.12-7.11 (d, 4H), 6.88-6.81 (m, 2H), 6.47-6.10 (q, 1H), 4.9 (s, 2H), 3.0 (s, 2H), 2.38 (b, 2H), 1.70 (b, 4H). Theoretic MS for C$_{21}$H$_{20}$F$_3$NO$_2$: 375.4; M$^+$+1 found, 376.1.

Synthesis of AX-117: Mixture of Compound D (0.25 g, 1 eq), K$_2$CO$_3$ (0.3 g, 3 eq), and N-methyl piperazine (0.11 g, 1.5 eq) in diisopropyl ether (15 ml) was heated at 60° C. for 2 h. The reaction was monitored by TLC. After completion, the mixture was poured into cold water (20 ml) and extracted with ethyl acetate (2×30 ml). The combined organic layer was washed with water (20 ml), saline solution (10 ml) and dried over anhydrous sodium sulfate. Purification of the crude product by column chromatography (8% methanol in DCM) yielded 40 mg of the desired product with a purity of 96.3% by HPLC. $^1$H NMR (DMSO-d$^6$) δ 7.32-7.30 (b, 2H), 7.22 (b, 2H), 7.13-6.76 (1H), 6.98-9.89 (2H), 6.2 (s, 1H), 4.88 (s, 2H), 2.91 (s, 3H), 2.67) b, 4H), 2.41 (b, 8H). Theoretic MS for C$_{22}$H$_{23}$F$_3$N$_2$O$_2$: 404.43; M$^+$+1 found, 405.1.

Synthesis of AX-118.HCl: Mixture of Compound D (0.2 g, 1 eq), K$_2$CO$_3$ (0.32 g, 4 eq), and N,N-dimethylethylenediamine (0.15 g, 3 eq) in diisopropyl ether (10 mL) was heated at 60° C. for 2 h. The reaction was monitored by TLC. After completion, the mixture was poured into cold water (20 ml) and extracted with ethyl acetate (2×25 ml). The combined organic layer was washed with water (20 ml), saline solution (10 ml) and dried over anhydrous sodium sulfate. Purification of the crude product by column chromatography (7% methanol in DCM) yielded 50 mg of the desired product with a purity of 92% by HPLC. The previous product was dissolved in dioxane (4 ml) and 0.5 ml of 4M HCl was added and stirred at RT. After 2 h, the filtration of the resulting solid, washed with 10 ml of n-pentane and vacuum dried, yielded 40 mg of pure product with a purity of 93% by HPLC. $^1$H NMR (DMSO-d$^6$) δ 10.7 (b, 1H), 9.76 (b, 2H), 7.42-7.34 (m, 4H), 7.17-6.98 (m, 3H), 6.26 (s, 1H), 5.04 (s, 2H), 3.6 (b, 2H), 3.3 (b, 2H), 2.79 (b, 6H). Theoretic MS for C$_{21}$H$_{24}$ClF$_3$N$_2$O$_2$: 428.88; M$^+$+1 found, 393.1 (—HCl).

Synthesis Scheme for AX-109 to AX-112

Synthesis of Compound B: A mixture of Compound A (3 g, 1 eq) sodium borohydride (0.17 g, 0.5 eq) in toluene (20 ml), methanol (2 ml) was added dropwise at RT and stirred at this temperature for 2 h. The reaction was monitored by TLC. After completion, the mixture was poured into cold water (100 ml) and extracted with ethyl acetate (2×30 ml). The combined organic layer was washed with water (20 ml), saline solution (10 ml) and dried over anhydrous sodium sulfate. Evaporation of the organic layer under reduced pressure yielded 2.7 g of the desired product. This material was taken directly to the next step without purification and analysis.

Synthesis of Compound C: To the mixture of Compound B (3.5 g, 1 eq), in toluene (30 ml), thionyl chloride (1.78 g, 1.4 eq) was added drop by drop at 0° C. and stirred for 2 h at RT 15, The reaction was monitored by TLC. After completion, the mixture is poured into iced water (25 ml) and extracted with ethyl acetate (2×25 ml). The combined organic layer was washed with water (30 ml), saline solution (10 ml) and dried over anhydrous sodium sulfate. Evaporation of the organic layer under reduced pressure (vacuum evaporation) yielded 34 g of crude product. This material was taken directly to the next step without purification and analysis.

Synthesis of AX-109: Mixture of Compound C (0.4 g, 1 eq), $K_2CO_3$ (0.5 g, 3 eq), and N-methyl piperazine (0.15 g, 1.2 eq) in ether diisopropyl (4 ml) was stirred at RT for 15 h. The reaction was monitored by TLC. Then poured into cold water (20 ml) and extracted with ethyl acetate (2×30 ml). The combined organic layer was washed with water (20 ml), saline solution (10 ml) and dried over anhydrous sodium sulfate. Purification of the crude product by column chromatography (5% methanol in DCM) yielded 170 mg of the desired product with a purity of 94.5% by HPLC. $^1$H NMR (CDCl$_3$) δ 7.10-7.09 (d, 4H), 6.82-6.79 (d, 1H), 6.68-6.65 (dd, 1H), 6.13 (d, 1H), 4.79 (s, 2H), 3.61 (s, 3H), 2.95 (s, 2H), 2.51-2.44 (b, 8H), 2.08 (s, 2H). Theoretic MS for $C_{22}H_{25}FN_2O_2$: 368.4; M$^+$+1 found, 369.2.

Synthesis of AX-110: Mixture of Compound C (0.4 g, 1 eq), $K_2CO_3$ (0.5 g 3 eq), and 10 N,N-dimethylethylenediamine (0.13 g, 1.2 eq.) in diisopropyl ether (4 ml) was stirred at RT for 15 h. The reaction was monitored by TLC. After completion the mixture was poured into cold water (20 ml) and extracted with ethyl acetate (2×30 ml). The combined organic layer was washed with water (20 ml), saline solution (10 ml) and dried over anhydrous sodium sulfate. Purification of the crude product made by the formation of HCl salt followed by neutralization using saturated sodium bicarbonate yielded 130 mg of the desired product with a purity of 94% by HPLC. NMR (CDCl$_3$) δ 7.17-7.08 (m, 4H), 6.82-6.80 (d, 1H), 6.67-6.65 (dd, 1H), 6.15-6.14 (d, 1H), 4.82 (s, 2H), 3.62 (s, 3H), 3.21 (s, 2H), 2.55-2.53 (t, 2H), 2.35-2.32 (t, 2H), 2.19 (s, 6H). Theoretic MS for $C_{21}H_{25}FN_2O_2$: 356.4; M$^+$+1 found, 357.1.

Synthesis of AX 111: Mixture of Compound C (0.4 g, 1 eq), $K_2CO_3$ (0.5 g, 3 eq) and morpholine (0.13 g, 1.2 eq) in diisopropyl ether (4 ml) was stirred at RT for 15 h. The reaction was monitored by TLC. After completion, the mixture was poured into cold water (20 ml) and extracted with ethyl acetate (2×30 ml). The combined organic layer was washed with water (20 ml), saline solution (10 ml) and dried over anhydrous sodium sulfate, Purification of the crude product made by crystallization using diethyl ether yielded 160 mg of the desired product with a purity of 96.5% purity by HPLC. $^1$H NMR (CDCl$_3$) δ 7.12-7.10 (d, 4H), 6.82-6.80 (d, 11-1), 6.68-6.65 (dd, 1H), 6.13 (d, 1H), 4.82 (s, 2H), 3.65-3.63 (m, 4H), 3.62 (s, 3H), 2.91 (s, 2H), 2.31 (b, 4H). Theoretic MS for $C_{21}H_{22}FNO_3$: 355.4; M$^+$+1 found, 356.1.

Synthesis of AX-112: Mixture of Compound C (0.4 g, 1 eq), $K_2CO_3$ (0.5 g, 3 eq), and ethylamine. HCl (0.12 g, 1.2 eq) in diisopropyl ether (4 ml) was stirred at RT for 15 h. The reaction was monitored by TLC. After completion the mixture was poured into cold water (20 ml) and extracted with ethyl acetate (2×30 ml). The combined organic layer was washed with water (20 ml), saline solution (10 ml) and dried over anhydrous sodium sulfate. Purification of the crude product by column chromatography (6% methanol in DCM) yielded 120 mg of the desired product with a purity of 95.0% by HPLC. NMR (CDCl$_3$) δ 7.26-7.09 (m, 4H), 6.82-6.80 (d, 1H), 6.68-6.65 (dd, 1H), 6.14 (d, 1H), 4.86 (s, 2H), 3.62 (s, 3H), 3.25 (s, 2H), 2.58-2.53 (m, 2H), 1.05-1.01 (t, 3H). Theoretic MS for $C_{19}H_{20}FNO_2$: 313.4; M$^+$+1 found, 269.2 (—NHEt).

Synthesis Scheme for AX-103 and AX-126 to AX-128

-continued

AX-126·HCl

AX-127·HCl

AX-128·HCl

Synthesis of Compound B: To mixture of Compound A (3.5 g, 1 eq) in toluene (30 ml), thionyl chloride (1.78 g, 1.4 eq) chloride was added drop by drop at 0° C. and stirred at RT for 2 h. The reaction was monitored by TLC. After completion, the mixture was poured into iced water (25 ml) and extracted with ethyl acetate (2×25 ml). The combined organic layer was washed with water (30 ml), saline solution (10 ml) and dried over anhydrous sodium sulfate. Evaporation of the organic layer under reduced pressure yielded 2.4 g of crude product. This material was taken directly to the next step without purification and analysis.

Synthesis of AX-103.HCl; The mixture of Compound B (0.2 g, 1 eq), $K_2CO_3$ (0.2 g 3 eq) and pyrrolidine (0.05 g, 1.2 eq) in diisopropyl ether (4 ml) was stirred at RT for 15 h. The reaction was monitored by TLC. After completion the mixture was poured into cold water (20 ml) and extracted with ethyl acetate (2×30 ml). The combined organic layer was washed with water (20 ml), saline solution (10 ml) and dried over anhydrous sodium sulfate. The crude product was converted into its HCl salt at a scale of 45 mg with a purity of 98.2% by HPLC. $^1$H NMR (CDCl$_3$) δ 7.26-7.20 (m, 2H), 7.17-7.14 (m, 2H), 7.14-7.06 (d, 1H), 6.95-6.93 (d, 1H), 6.41-6.40 (d, 1H), 5.29 (s, 2H), 3.72-3.66 (m, 4H). Theoretic MS for $C_{21}H_{23}ClF_4N_2O_2$: 429.84; M$^+$+1 found, 394.1 (—HCl).

Synthesis of AX-126.HCl: The mixture of Compound B (0.4 g, 1 eq). $K_2CO_3$ (0.5 g, 3 eq) and N,N-dimethylethylenediamine (0.13 g, 1.2 eq.) in diisopropyl ether (4 ml) was stirred at RT for 15 h. The reaction was monitored by TLC. After completion the mixture was poured into cold water (20 ml) and extracted with ethyl acetate (2×30 ml). The combined organic layer was washed with water (20 ml), saline solution (10 ml) and dried over anhydrous sodium sulfate. Purification of the crude product made by formation of the HCl salt yielded 60 mg of the desired product with a purity of 93.7% purity by HPLC. $^1$H NMR (DMSO-d$^6$) δ 10.8 (b, 1H), 9.70 (b, 1H), 7.93-7.92 (b, 2H), 7.30-7.24 (m, 2H), 7.19-7.11 (m, 2H), 7.01-6.96 (m, 2H), 6.87-6.85 (d, 1H), 6.3 (s, 1H), 5.0 (s, 2H), 3.55 (s, 2H), 3.40 (b, 2H), 2.78 (b, 6H) Theoretic MS for $C_{21}H_{23}ClF_4N_2O_2$: 446.87; M$^+$+1 found, 411.1 (—HCl).

Synthesis of AX-127; The mixture of Compound B (0.4 g, 1 eq), $K_2CO_3$ (0.5 g, 3 eq) and morpholine (0.13 g, 1.2 eq) in diisopropyl ether (4 ml) was stirred at RT for 15 h. The reaction was monitored by TLC. After completion the mixture was poured into cold water (20 ml) and extracted with ethyl acetate (2×30 ml). The combined organic layer was washed with water (20 ml), saline solution (10 ml) and dried over anhydrous sodium sulfate. It was evaporated under reduced pressure (vacuum evaporation) to yield 110 mg of the desired product with a purity of 96% by HPLC. $^1$H NMR (CDCl$_3$) δ 7.16-7.08 (m, 4H), 6.97-6.95 (d, 1H), 6.85-6.83 (d, 1H), 6.40-6.39 (b, 1H), 4.90 (s, 2H), 3.66-3.64 (t, 4H), 2.92 (s, 2H), 2.31 (b, 4H). Theoretic MS for $C_{21}H_{19}F_4NO_3$: 409.3; M$^+$+1 found, 410.1.

Synthesis of AX-128,HCl: The mixture of Compound B (0.4 g, 1 eq,), $K_2CO_3$ (0.5 g, 3 eq) and ethylamine. HCl (0.12 g, 1.2 eq.) in diisopropyl ether (4 ml) was stirred at RT for 1 h. The reaction was monitored by TLC. After completion, the mixture was poured into cold water (20 ml) and extracted with ethyl acetate (2×30 ml). The combined organic layer was washed with water (20 ml), saline solution (10 ml) and dried over anhydrous sodium sulfate. Purification of the crude product made by formation of HCl salt yielded 65 mg of the desired product with a purity of 98.2% by HPLC. $^1$H NMR (CDCl$_3$) δ 7.27-7.24 (m, 2H), 7.21-7.16 (m, 2H), 7.04-7.01 (m, 1H), 6.86-6.84 (d, 1H), 6.44-6.43 (b, 1H), 5.13 (s, 2H), 3.58-3.55 (t, 2H), 2.91-2.87 (m, 2H). Theoretic MS for $C_{19}H_{18}ClF_4NO_2$: 405.8; M$^+$+1 found, 368.1 (HCl).

Example 2: Inhibition of T Cell Proliferation Induced by TCR Stimulation

Figure 1:
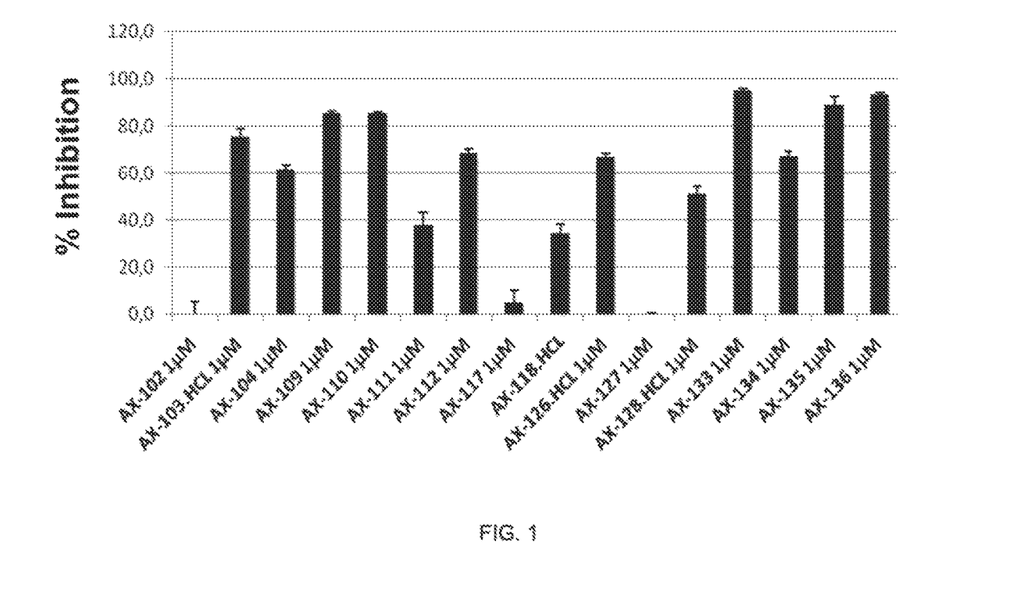
FIG. 1. Represents the ability of inhibiting the proliferation of T lymphocytes for each of the tested compounds of the invention.

The effect of compounds AX-101, AX-103HCl; AX-104, AX-109, AX-110, AX-111, AX-127, AX-133, AX-135 and AX-136 on the capacity of the TCR to induce T lymphocyte proliferation was assessed in primary T lymphocytes obtained from blood of healthy human donors (PBMC, peripheral blood mononuclear cells). PBMC of the volunteers were isolated from venous blood by centrifugation in Ficoll-Paque Plus density gradients. Purified cells (NWT; Nylon Wood T cells) were cultured in triplicate in 96-well plates (0.5×10$^5$/well) in 200 ul of complete medium and stimulated with OKT3 (10 ug/ml) or with OKT3 (10 ug/ml) plus CD28 in the presence or absence of different concentrations of compounds 1 and 10 uM. The cultures were incubated for three days and analyzed after addition of 0.5 uCi [3H]TdR/well for the last 12 h of the culture. The radioactivity incorporated into DNA was determined by liquid scintillation counting. As cells divide, radioactivity is incorporated into daughter cells which it gives an idea of the degree of cell proliferation. The inhibition capacity of the tested compounds is shown in FIG. 1.

Example 3: Improving the Bioavailability of the Compound AX-104 after Oral Administration in Rodents The pharmacokinetic properties of the compound AX-104 were analyzed in relation to those observed for compound ECRA-24 (described in WO2012/042078). For this, intravenous administration of the compound (bolus) and oral gavage of a solution of the compounds was performed separately in rats (mean±SD; n=3). As seen in the data shown in Tables 1 and 2, the total bioavailability of the compound AX-104 after oral administration was 24% compared to that of 2% of ECRA-24.

TABLE 1

Pharmacokinetic parameters means of ECRA-24 in Swiss albino mice.

| Route | Dose (mg/kg) | $T_{max}$ (h) | $C_{max}$ (ng/mL) | $AUC_{last}$ (ng · h/mL) | $AUC_{int}$ (ng · h/mL) | CL (mL/min/kg) | $V_{ss}$ (L/kg) | $T_{1/2}$ (h) | F [a] |
|---|---|---|---|---|---|---|---|---|---|
| IV | 5 | NA | 1168.89 | 838.43 | 840.27 | 99.17 | 11.37 | 3.36 | — |
| PO | 50 | 0.25 | 171.56 | 297.03 | 299.69 | NA | NA | 4.93 | 4 |

TABLE 2

Pharmacokinetic parameters means of AX-104 in Swiss albino mice.

| Route (Dosis) | Analite | $T_{max}$ (h) | $C_{max}$ (ng/mL) | $AUC_{last}$ (ng · h/mL) | $AUC_{inf}$ (ng · h/mL) | CL (mL/min/kg) | $V_{ss}$ (L/kg) | $T_{1/2}$ (h) | F [b] |
|---|---|---|---|---|---|---|---|---|---|
| IV (5 mg/kg) | AX-04 | NA | 1281.10 [c] | 723.92 | 749.72 | 111.15 | 20.64 | 8.45 | NA |
| PO (50 mg/kg) | AX-104 | 0.25 | 930.20 | 1759.86 | 1793.43 | NA | NA | NA | 24 |

Example 4: In Vivo Test on Model of EAE (Experimental Autoimmune Encephalomyelitis)

Figure 2:
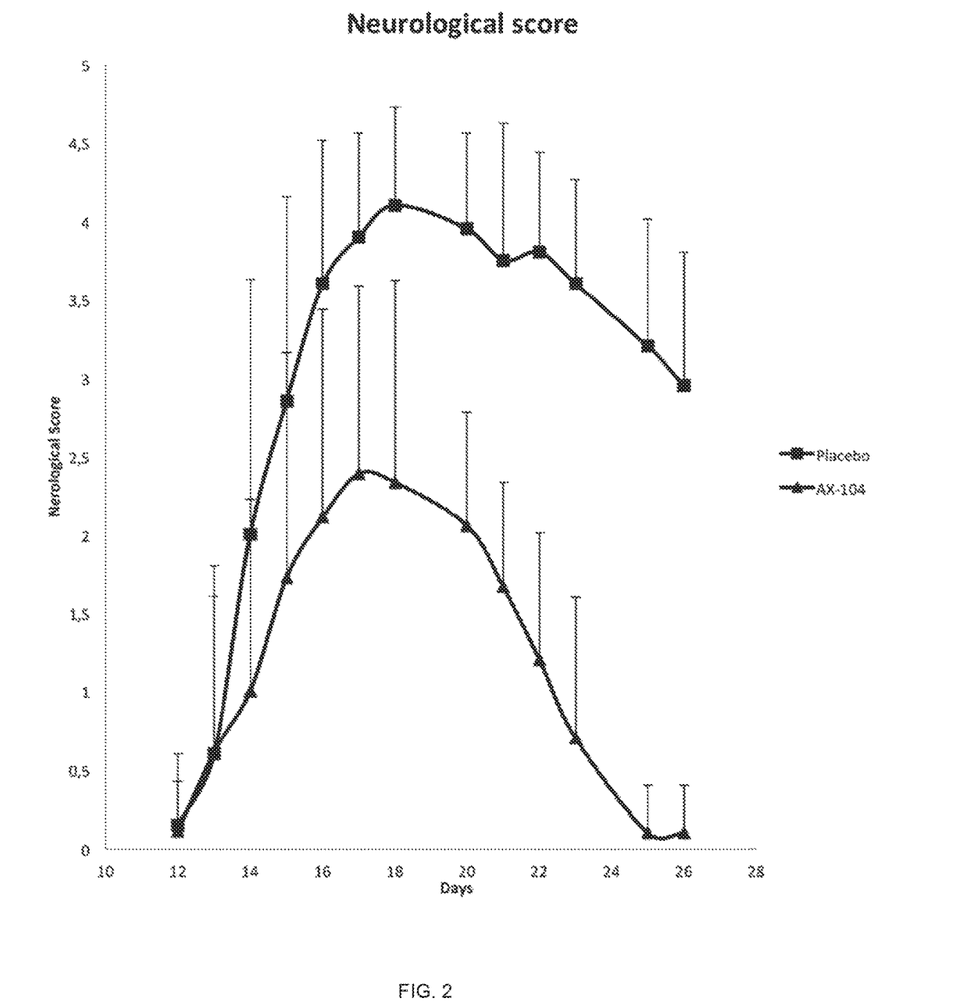
FIG. 2. Represents an estimation of the level of neuronal damage during the study among the subjects receiving placebo and those receiving the compound AX-104.

The model of chronic EAE was induced in 10 C57BL/6 female mice per treatment group (6-8 weeks old, 20 g body weight) by subcutaneous injection of a total of 150 μg of peptide MOG (Myelin Oligodendrocyte Glycoprotein; MOG35-55, Espikem, Germany) emulsified in Freund's Complete Adjuvant (CFA, Sigma-Aldrich) and supplemented with 5 mg/ml of Mycobacterium tuberculosis (H37Ra strain of Difco) in both femoral regions. The mice were immediately injected intraperitoneally with 150 ng of pertussis toxin (Sigma-Aldrich) and once more, 48 h after immunization. The compound indicated (AX-104) was prepared in a saline buffer and administered orally during the first 10 days starting on the same day of immunization. Subjects on the placebo group received an equivalent oral dose containing simply saline buffer. Animals were weighed and clinical signs of the disease were analyzed by an external observer out of the process by means of visual analysis of the symptoms based on the following scale; 0=normal; 1=weak limp tail or slight limp of hind limbs; 2=moderate hind limb weakness or mild ataxia; 3=moderately severe weakness in hind limbs: 4=severe hindlimb weakness or mild forelimb weakness or moderate ataxia; 5=paraplegia with nothing more than moderate forelimb weakness; and 6=paraplegia with severe forelimb weakness or severe ataxia, moribund condition or death. FIG. 2 shows how the animals receiving compound AX-104 present a reduced score when compared to the placebo group.

Figure 3:
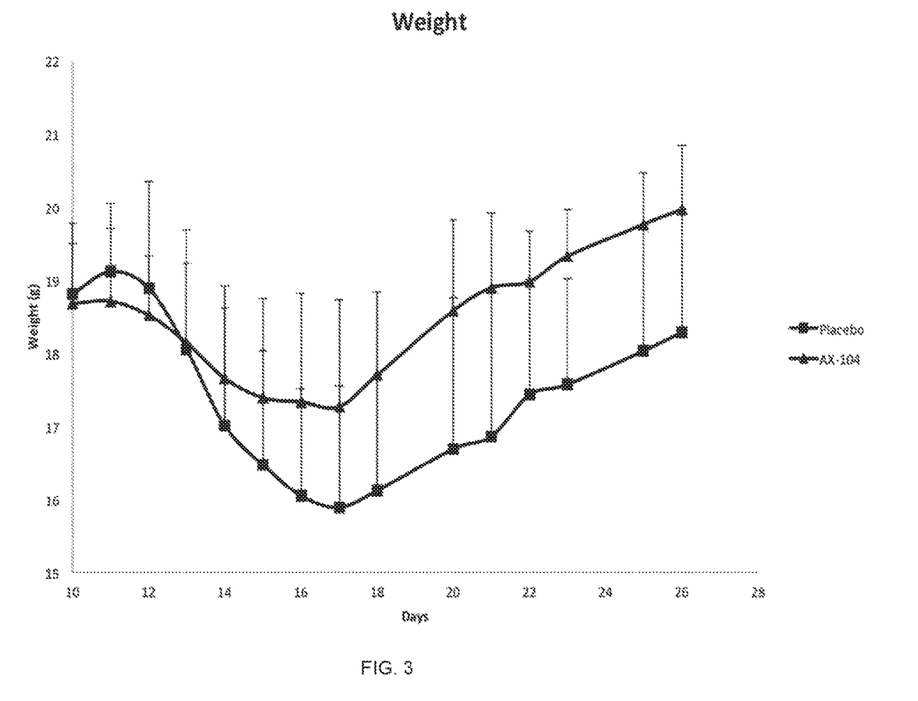
FIG. 3. Represents weight progression during the study among the subjects receiving placebo and those receiving the compound AX-104.

In parallel, the weight of the animals was also monitored as a measurement indicative of the general welfare of the animals and evolution of the disease. FIG. 3 shows that treated animals present a weight loss significantly reduced when compare to animals on the placebo group.

At the end of the study, the animals were anesthetized and an intra-cardiac perfusion was performed with 4% paraformaldehyde in 0.1 M phosphate buffer (pH 7.6). The brain and spinal cords of mice was dissected and fixed.

Results overall show that compound AX-104 is capable of significantly reducing the impact of the symptoms associated to the model.

Example 5: In Vitro Test on Blood Cells

Human peripheral blood mononuclear cells (PBMC) from healthy adult volunteer donors were isolated from venous blood by centrifugation in Ficoll-Paque Plus density gradients. Purified T cells (NWT-0.5×10⁵/well) are cultured in triplicate in 96-well plates in 200 ul of complete medium and stimulated with OKT3 (10 ug/ml) or with OKT3 (10 ug/ml) and CD28 in presence or absence of test compounds at the desired concentrations. The cultures were grown for three days and a pulse of 0.5 uCi of [$^3$H] TdR/well is administered during the last 12 h of culture. The radioactivity incorporated in the DNA was assessed by liquid scintillation counting.

The invention claimed is:

1. A compound having the structure of formula (I)

or a pharmaceutically acceptable salt thereof, wherein:
$R_1$ is $C_1$-$C_4$ alkyl substituted by $C_3$-$C_6$ cycloalkyl;
$R_2$ and $R_3$ are each independently selected from hydrogen, and substituted or not substituted $C_1$-$C_6$ alkyl; or $R_2$ and $R_3$ form, together with the nitrogen atom they are bound to, substituted or not substituted saturated 5- or 6-membered heterocycle;
$R_4$ is halogen.

2. The compound according to claim 1 wherein $R_1$ is methyl substituted by $C_3$-$C_6$ cycloalkyl.

3. The compound according to claim 1 wherein $R_1$ is $C_1$-$C_4$ alkyl substituted by cyclopropyl.

4. The compound according to claim 1 wherein $R_1$ is —$CH_2$-cyclopropyl.

5. The compound according to claim 1 wherein $R_2$ and $R_3$ form, together with the nitrogen atom they are bound to, a not substituted saturated 5-membered heterocycle.

6. The compound according to claim 1 wherein $R_2$ and $R_3$ form, together with the nitrogen atom they are bound to, a not substituted saturated 6-membered heterocycle.

7. The compound according to claim 6 wherein the not substituted saturated 6-membered heterocycle contains an additional N or O atom.

8. The compound according to claim 1 wherein $R_2$ is —H.

9. The compound according to claim 8 wherein $R_3$ is substituted or not substituted $C_1$-$C_4$ alkyl.

10. The compound according to claim 9 wherein $R_3$ is —$CH_2CH_3$.

11. The compound according to claim 9 wherein $R_3$ is a $C_1$-$C_4$ alkyl group substituted by an —NR'R" group, wherein R' and R" are independently H or $C_1$-$C_4$ alkyl.

12. The compound according to claim 11 wherein $R_3$ is —$CH_2$—$CH_2$—$N(CH_3)_2$.

13. The compound according to claim 5 wherein the not substituted saturated 5-membered heterocycle is pyrrolidinyl.

14. The compound according to claim 1 wherein $R_2$ and $R_3$ form, together with the nitrogen atom they are bound to, substituted saturated 6-membered heterocycle.

15. The compound according to claim 14 wherein the saturated 6-membered heterocycle is substituted by $C_1$-$C_4$ alkyl in at least one of its positions.

16. The compound according to claim 14 wherein the 6-membered saturated heterocycle contains an additional N or O atom.

17. The compound according to claim 16 wherein the N atom is substituted by $C_1$-$C_4$ alkyl.

18. The compound according to claim 16 wherein the 6-membered saturated heterocycle is 19. The compound according to claim 1 wherein $R_4$ is fluorine.

20. The compound of formula (I) according to claim 1 which is selected from the group consisting of:
1-((6(cyclopropylmethoxy)4-(4-fluorophenyl)-2H-chromen-3-yl)methyl)pyrrolidine,
1-(6-(cyclopropylmethoxy)-4-(4-fluorophenyl)-2H-chromen-3-yl)methyl)-4-methylpiperazine,
$N^1$-((6-(cyclopropylmethoxy)-4-(4-fluorophenyl)-2H-chromen-3-yl)methyl)-$N^2$,$N^2$-dimethylethane-1,2-diamine,
4-((6-(cyclopropylmethoxy)-4-(4-fluorophenyl)-2H-chromen-3-yl)methyl)morpholine, and
N-((6-(cyclopropylmethoxy)-4-(4-fluorophenyl)-2H-chromen-3-yl)methyl)ethanamine.

21. A pharmaceutical composition comprising a compound of formula (I) according to claim 1 and one or more pharmaceutically acceptable excipients.

22. The compound according to claim 7 wherein the not substituted saturated 6-membered heterocycle is

* * * * *

UNITED STATES PATENT AND TRADEMARK OFFICE
CERTIFICATE OF CORRECTION

PATENT NO. : 10,131,647 B2
APPLICATION NO. : 15/029042
DATED : November 20, 2018
INVENTOR(S) : Andrés Gagete Mateos et al.

Page 1 of 1

It is certified that error appears in the above-identified patent and that said Letters Patent is hereby corrected as shown below:

On the Title Page

In Column 1, item (73) Assignee, "Artex Biopharma Inc." should read --Artax Biopharma Inc.--.

Signed and Sealed this
Fifth Day of February, 2019

Andrei Iancu
*Director of the United States Patent and Trademark Office*